United States Patent [19]

Rajamannan

[11] Patent Number: 4,941,991

[45] Date of Patent: Jul. 17, 1990

[54] COMPOSITION AND PROCESS FOR USE IN NEUTRALIZING MALODOROUS GASES

[76] Inventor: A. H. J. Rajamannan, 2120 Argonne Dr., N.E., Minneapolis, Minn. 55421

[21] Appl. No.: 111,414

[22] Filed: Oct. 22, 1987

[51] Int. Cl.$^5$ .............................................. C09K 3/00
[52] U.S. Cl. ................................ 252/189; 252/183.13; 252/183.11
[58] Field of Search ................ 252/189, 193; 524/391; 423/226, 236, 228, 243

[56] References Cited

U.S. PATENT DOCUMENTS 4,708,854 11/1987 Grinstead ............................ 423/239

FOREIGN PATENT DOCUMENTS 62-225244 10/1987 Japan .

*Primary Examiner*—Paul Lieberman
*Assistant Examiner*—John F. McNally

[57] ABSTRACT

A composition for neutralizing malodorous odors and a method of using the same including a compound which includes a neutralizing agent and a solvent. The neutralizing agent consists of either unsubstituted or substituted polyethyleneimine. The solvent consists of water or a lower alkanol. It is preferred that the neutralizing compound include a cross-linking agent and a surfactant for efficient contact with offensive gas. The neutralizing compound, when sprayed into an environment containing malodorous gases, such as hydrogen sulphide, sulphur dioxide, aldehydes, ketones, ammonia, mercaptans, or the like, immediately cross-links with and neutralizes the malodorous gas.

2 Claims, No Drawings

COMPOSITION AND PROCESS FOR USE IN NEUTRALIZING MALODOROUS GASES

This invention relates to a composition and process for neutralizing air permeated malodorous gases, such as hydrogen sulphide, sulphurdioxide, aldehydes, ketones, ammonia, mercaptans, and the like.

BACKGROUND OF THE INVENTION

Air pollution is one of the large environmental problems confronting society today. While some of the pollutants are injurious to health, other air pollutants are simply offensive as bad odors, especially in local areas. The advances made in the control of such bad odors involve the application of heavy scented sprays used to mask the odors. Another means of controlling offensive odors is to absorb the gas as the malodorous gas is passed through charcoal filters.

SUMMARY OF THE INVENTION

An object of this invention is to provide a composition and method of using the same for neutralizing malodorous gases, such as hydrogen sulphide, sulphurdioxide, aldehydes, ketones, ammonia, mercaptans, and the like. This novel composition, when applied as a spray to air permeated with malodorous gases, serves to neutralize the gas by crosslinking the gas molecules with polyethyleneimine. In carrying out this invention, the liquid spray composition consists of unsubstituted polyethyleneimine or substituted polyethyleneimine in a solvent, such as water or lower alkanols, and is provided with a wetting agent or surfactant. It has also been found that the composition may not only be sprayed in polluted air, but also can be applied directly to the source of pollutant or to the fibers of fibrous filters through which air is circulated in air conditioning systems.

DESCRIPTION OF THE PREFERRED EMBODIMENT

In the present invention, malodorous gases can be neutralized by cross-linking the gaseous molecules with polyethyleneimine. If the malodorous gases are dispersed in the air, the polyethyleneimine can be applied as a spray and is dissolved in water or a lower alkanol, such as ethanol, methanol, isopropanol, or the like. The malodorous gases can be made more easily soluble with respect to the polyethyleneimine solution by adding a wetting agent or surfactant to the solution.

Polyethyleneimine can be graphically depicted as being of the general formula $(-CH_2-CH_2-NH-)_x$. These are well-known substances available, with molecular weights ranging from about 300 to about 100,000. The polyethyleneimine can be unsubstituted, or one can also employ various modified derivatives thereof in which pendant groups, such as alkyl, phenylalkyl, cyanoalkyl, or carbamyl groups, are bound to some or all of the imine groups, or to the terminal amine groups. For example, such derivatives include those obtained upon treating polyethyleneimine with alkylene oxides, such as ethylene oxide, so as to yield a hydroxyalkylated polyethyleneimine; those obtained with epichlorohydrin so as to yield epoxyalkylated and/or hydroxychloroalkylated polyethyleneimine; phenylalkyl derivatives, such as, for example, poly-N (2 phenethyl) aziridine; 2-cyanethyl modified polyethyleneimine; urea modified polyethyleneimine; the polyethyleneimine obtained upon treatment with a sulfonated epichlorohydrin so as to yield an amphoteric hydroxysulfoalkyl substituted polyethyleneimine, and other modified derivatives.

Therefore, respresentative of the polyethyleneimine used in the gas neutralizing composition are the unsubstituted polyethyleneimine (PEI) of molecular weight from 300 to 100,000; hydroxyethylated PEI; alkoxylated PEI wherein the ratio of alkylene oxides to the polyethyleneimine varies from 0.1:1 to 10:1; epichlorohydrin modified PEI; poly-N (2 phenethyl) aziridine; poly-N-(2-cyanoethyl) aziridine; urea modified PEI, obtained as a reaction product of PEI and urea; amphoteric PEI prepared from the reaction of PEI with -chloro-2-hydroxypropane sulfonate; quarternized PEI having a percentage of quarternization of from 25% to 75% PEI 600.

In the preferred embodiment, the unsubstituted polyethyleneimine or the modified derivative thereof is dissolved in a water or alkanol base in the presence of a wetting agent or surfactant. For example, any of the well-known commercial surfactants may be used, such as ethylene oxide, condensate sold under the Trademark "TRITON", manufactured by Rohm & Haas; nonyl phenol ethylene oxide condensate, sold under the Trademark "TERGITOL", manufactured by Union Carbide; linear primary alcohol ethylates, sold under the Trademark "NEODOL", manufactured by Shell Chemical Company.

It is also preferred that a cross-linking agent be added, such as zinc ammonium carbonate or ammonium dichromate. Other cross-linking agents or a cross-linking reagent, such as an epoxide, including glycerol expoxy resins, polycycloaliphatic polyepoxides and similar epoxides, may also be used. The amount of cross-linking or promoting agent can be as low as 0.001:2 parts of the polyethyleneimine.

The neutralizing polyethyleneimine compound may be first prepared as a concentrate and may thereafter be diluted in accordance with the requirements for the specific application. For example, in low odor (non-intense) environments, a more dilute mixture of the concentrate and solvent will be used than the application of the neutralizing agent to a high odor (intense concentration of bad odors) environment. In this regard, the polyethyleneimine concentrate may be diluted 1:10 parts when applied to high odor environments and up to 1:200 parts in very low odor situtations.

It is also pointed out that the polyethyleneimine neutralizing agent can be applied directly to the source emanating the malodorous gases. If the offensive gases are being liberated from a liquid, the polyethyleneimine neutralizing agent can be applied directly to the surface of the liquid. The malodorous molecules will be crosslinked with the polyethyleneimine as the gas is liberated.

The neutralizing polyethyleneimine may also be applied to the fibers of fibrous filters used in air conditioners and cleaning systems. In this regard, the polyethyleneimine solution or concentrate may be sprayed directly on the fibers of fibrous filters and will cross-link and neutralize offensive odors entrained in the air and passing through the filter.

It has also been found that the polyethyleneimine neutralizing composition is also effective in reducing malodorous gases generated in fires. In this regard, polyethyleneimine neutralizing composition may be added to water sprays or other compatible chemical sprays used as fire fighting materials. The polyethyleneimine neutralizing composition has been found to neutralize toxic gases which are generated during fires.

The following examples are merely illustrative of the use of the neutralizing compound and should not be construed as limiting the scope of the invention.

| PEI 1800 MW ethylene oxide modified (1:1) | 40% |
| --- | --- |
| Ethanol 1% in water | 59% |
| Zinc ammonium carbonate | 1% |

The above ingredients were mixed together for use as a concentrate. The concentrate was diluted 1:10 parts when applied to high (intense) odor situations and up to 1:200 parts in very low odor situations. When the diluted neutralizing compound was applied to an environment where both high and low odors occurred, the neutralizing compound immediately neutralized the odors.

| PEI (300 MW) unmodified | 20% |
| --- | --- |
| Surfactant | 20% |
| Water | 58% |
| Cross-linking agent glycerol epoxy resin | 2% |

The ingredients in this example were mixed and used as a concentrate. The concentrate was diluted between 1:10 parts and 1:200 parts of water for application as an aerosol or fine mist in a malodorous environment. When the diluted neutralizing compound was applied to a malodorous environment, where both high and low odors occurred, the neutralizing compound immediately neutralized the odors. The diluted concentrate (dilution preferably 1:10) was sprayed on a fiber mesh of an air filter through which malodorous odors passed. The odors in the air passing through the filter were immediately neutralized by the neutralizing compound.

Example III

| PEI 1800 MW urea modified | 20% |
| --- | --- |
| Surfactant (ethyleneoxide) | 20% |
| Water | 56% |
| Ethanol | 2% |
| Glycerol epoxy resin | 2% |

The above ingredients were mixed together for use as a concentrate. The concentrate was diluted with water in the manner of Example I and applied to a malodorous environment containing both high and low odors, and these odors were immediately neutralized by the neutralizing compound.

What is claimed is:

1. A composition for neutralizing malodorous gases in the air, comprising:

a gas neutralizing agent selected from the group consisting of unsubstituted polyethyleneimine having a molecular weight of from about 300 to about 100,000 and substituted polyethyleneimines modified through substitution of hydroxyalkyl, hydroxychloroalkyl, epoxyyalkyl, hydroxy sulfoalkyl, phenylalkyl, cyanoalkyl, and carbamyl groups on at least one of said imine groups of the polyethyleneimine, a solvent including water and lower alkanols selected from the group consisting of ethanol, methanol, and isopropanol, said neutralizing agent comprising 20% to 40% by weight, said water comprising approximately 56% to 58% by weight, and said lower alkanol comprising approximately 2% by weight of said composition, a cross-linking agent for cross-linking polyethyleneimine with the molecules of malodorous gas selected from the group consisting of ammonium dichromate, glycerol epoxy resins, and polycycloaliphatic polyepoxides, the amount of cross-linking agent comprising about 0.001 part to 2 parts based on the total weight of the unsubstituted or substituted polyethyleneimine, and said composition being diluted between 1:10 and 1:200 parts water and applied as a spray or mist, into the air containing malodorous gases.

2. The composition as defined in claim 1 including a surfactant.

* * * * *